(12) United States Patent
Tropper et al.

(10) Patent No.: US 8,177,260 B2
(45) Date of Patent: May 15, 2012

(54) COUPON REDEEMABLE UPON COMPLETION OF A PREDETERMINED THRESHOLD OF PHYSICAL ACTIVITY

(75) Inventors: Seth A. Tropper, Marlboro, NJ (US);
Amado Batour, Somerset, NJ (US);
James Wickstead, Mendham, NJ (US);
John Gardner, Mullica Hill, NJ (US)

(73) Assignee: Switch2Health Inc., North Brunswick, NJ (US)

( * ) Notice: Subject to any disclaimer, the term of this patent is extended or adjusted under 35 U.S.C. 154(b) by 995 days.

(21) Appl. No.: 11/862,059

(22) Filed: Sep. 26, 2007

(65) Prior Publication Data

US 2008/0093838 A1    Apr. 24, 2008

Related U.S. Application Data

(60) Provisional application No. 60/847,538, filed on Sep. 26, 2006.

(51) Int. Cl.
*B42D 1/00* (2006.01)
*B42D 19/00* (2006.01)
*B42D 15/00* (2006.01)
*G09B 19/00* (2006.01)

(52) U.S. Cl. .............. 283/67; 281/2; 281/5; 283/51; 283/52; 283/61; 283/62; 283/72; 283/81

(58) Field of Classification Search .............. 281/2, 5, 281/15.1, 51; 283/61, 62, 63.1, 72, 117, 283/51, 52, 56, 67, 81; 402/80 R
See application file for complete search history.

(56) References Cited

U.S. PATENT DOCUMENTS

| | | | |
|---|---|---|---|
| 3,163,856 A | 12/1964 | Kirby | |
| 3,918,658 A | 11/1975 | Beller | |
| 4,281,663 A | 8/1981 | Pringle | |
| 4,390,922 A | 6/1983 | Pelliccia | |
| 4,407,295 A | 10/1983 | Steuer et al. | |
| 4,617,525 A | 10/1986 | Lloyd | |
| 5,446,705 A | 8/1995 | Haas et al. | 368/327 |
| 5,456,648 A | 10/1995 | Edinburg et al. | 482/4 |
| 6,077,193 A | 6/2000 | Buhler et al. | |
| 6,129,686 A | 10/2000 | Friedman | |
| 6,213,872 B1 | 4/2001 | Harada et al. | 463/7 |
| 6,302,789 B2 | 10/2001 | Harada et al. | 463/7 |
| 6,469,639 B2 | 10/2002 | Tanenhaus et al. | |

(Continued)

FOREIGN PATENT DOCUMENTS

WO    WO 2008/038141    4/2008

(Continued)

OTHER PUBLICATIONS

ISR issued Aug. 15, 2008, in conjunction with related application PCT/IB07/03617.

(Continued)

*Primary Examiner* — Dana Ross
*Assistant Examiner* — Justin Lewis
(74) *Attorney, Agent, or Firm* — Pillsbury Winthrop Shaw Pittman LLP

(57) ABSTRACT

A coupon for providing an incentive for a user to participate in physical activity. The coupon detects the physical activity of a user and indicates to the user when the threshold of physical activity has been reached. Once the coupon has indicated that the threshold has been reached, the user may redeem the coupon for a reward.

24 Claims, 15 Drawing Sheets

U.S. PATENT DOCUMENTS

| | | | |
|---|---|---|---|
| 6,561,951 B2 | 5/2003 | Cannon et al. | 482/1 |
| 6,585,622 B1 | 7/2003 | Shum et al. | |
| 6,607,493 B2 | 8/2003 | Song | |
| 6,699,188 B2 | 3/2004 | Wessel | |
| 6,808,473 B2 | 10/2004 | Hisano | |
| 6,811,516 B1 | 11/2004 | Dugan | 482/8 |
| 6,813,931 B2 | 11/2004 | Yadav et al. | |
| 6,862,575 B1 | 3/2005 | Anttila et al. | 705/14.14 |
| 7,272,982 B2 * | 9/2007 | Neuhauser et al. | 283/72 |
| 7,443,292 B2 * | 10/2008 | Jensen et al. | 281/51 |
| 2001/0055242 A1 | 12/2001 | Deshmukh et al. | |
| 2002/0013717 A1 | 1/2002 | Ando et al. | |
| 2002/0077219 A1 | 6/2002 | Cohen et al. | |
| 2002/0109600 A1 | 8/2002 | Mault et al. | |
| 2002/0178060 A1 | 11/2002 | Sheehan | 705/14 |
| 2002/0198776 A1 | 12/2002 | Nara et al. | |
| 2003/0018523 A1 | 1/2003 | Rappaport et al. | 705/14 |
| 2003/0050537 A1 | 3/2003 | Wessel | |
| 2003/0065561 A1 | 4/2003 | Brown et al. | |
| 2004/0152957 A1 * | 8/2004 | Stivoric et al. | 600/300 |
| 2005/0037844 A1 * | 2/2005 | Shum et al. | 463/36 |
| 2005/0038679 A1 | 2/2005 | Short | |
| 2005/0102172 A1 | 5/2005 | Sirmans, Jr. | |
| 2005/0228692 A1 | 10/2005 | Hodgdon | |
| 2005/0234742 A1 | 10/2005 | Hodgdon | |
| 2005/0272564 A1 | 12/2005 | Pyles et al. | |
| 2006/0025282 A1 | 2/2006 | Redmann | 482/8 |
| 2006/0047447 A1 | 3/2006 | Brady et al. | |
| 2006/0089542 A1 | 4/2006 | Sands | |
| 2006/0111944 A1 | 5/2006 | Sirmans, Jr. et al. | |
| 2006/0129436 A1 | 6/2006 | Short | |
| 2006/0277474 A1 | 12/2006 | Robarts et al. | 715/745 |
| 2006/0287883 A1 | 12/2006 | Turgiss et al. | |
| 2007/0136093 A1 | 6/2007 | Rankin et al. | |
| 2007/0179356 A1 | 8/2007 | Wessel | |
| 2009/0171788 A1 | 7/2009 | Tropper et al. | 705/14 |

FOREIGN PATENT DOCUMENTS

| | | |
|---|---|---|
| WO | WO 2009/042965 | 4/2009 |

OTHER PUBLICATIONS

In U.S. Appl. No. 12/239,613, a non-final Office Action was mailed on Aug. 16, 2011, 17 pages.

* cited by examiner

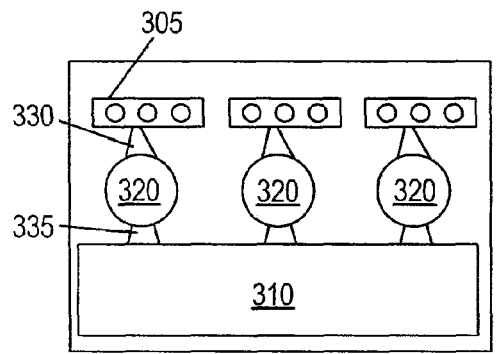
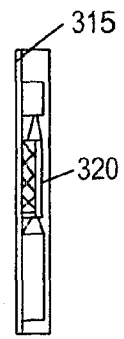
FIG. 3a    FIG. 3b
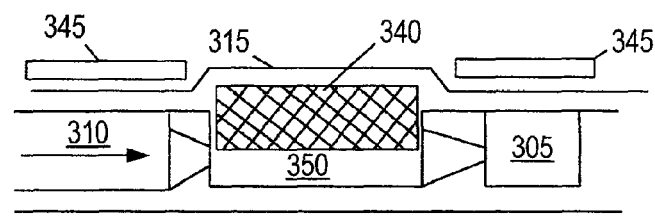
FIG. 3c

COUPON REDEEMABLE UPON COMPLETION OF A PREDETERMINED THRESHOLD OF PHYSICAL ACTIVITY

This application claims the benefit of U.S. Provisional Patent Application Ser. No. 60/847,538, entitled "Kinetic Coupon Redeemable Upon Completion of a Predetermined Threshold of Physical Activity," filed on Sep. 26, 2006, the contents of which are hereby incorporated by reference in their entirety. In addition, this application is related to U.S. patent application Ser. No. 12/239,613, entitled "System and Method for Activating a Device Based on a Record of Physical Activity," filed on Sep. 26, 2008, which is a continuation-in-part of the present application.

BACKGROUND OF THE INVENTION

The present application is directed to a system and method for encouraging physical activity and in particular a system and method for utilizing a coupon to indicate the achievement or completion of physical activity for a predetermined amount and/or predetermined period of time.

Obesity has taken a front seat in public discussions and media coverage. As a nation, we have been getting steadily heavier. The number of adults who are obese has increased dramatically. An estimated 300,000 deaths each year in the United States are attributed to obesity. The economic cost of obesity in the United States was approximately $117 billion in year 2000. Obesity has reached epidemic proportions in the United States, as well as worldwide. According to national data analyzed in 2002, it is estimated that 65% of Americans are now overweight or obese, and more than 61 million adults are obese.

Adults are not the only ones who have been getting heavier. The percentage of overweight children in the United States is growing at an alarming rate, specifically, it has more than doubled since the 1970s. Children are spending less time exercising and more time in front of the television, computer, or video-game consoles. According to the Center for Disease Control, 16% (or ~9 million) of American children are substantially overweight and the number is expected to grow by 20% over the next 5 years. Some states have childhood obesity rates as high as 25%. Children who lack exercise and proper nutrients in their diet are subject to an increased risk of potential serious health related problems including stunted growth, cognitive impairment, heart disease, diabetes and a range of other illnesses.

The United States Department of Health and Human Services recommends that children and teens be physically active for at least 60 minutes on most, if not all, days. It is recommended that adults engage in at least 30 minutes of moderate-intensity physical activity, above usual activity, on most days of the week. More than 60% of adults do not achieve the recommended amount of regular physical activity. In fact, 25% of the adults in the United States do not participate in any leisure time physical activity. Physical activity declines dramatically with age during adolescence. As such, nearly 50% of young people aged 12-21 are not active on a regular basis. Physical activity is important in preventing and treating obesity and is extremely helpful in maintaining weight loss, especially when combined with a healthy diet.

Exercise is one component of the equation to solve the problem of obesity. The real challenge is motivating individuals to participate in an exercise regimen or physical activity. People's behavior must change and they must lead a lifestyle of physical activity. Corporations have become sensitive to the perception that they are socially responsible. As such, corporations strategically advertise and promote their contributions towards a healthy community and encourage physical activity. Numerous fast food restaurants have dramatically altered their menus to incorporate healthy foods thereby promoting the importance of healthy lifestyles and physical fitness.

Exercise, while rewarding in numerous ways, offers little incentive or motivation for individuals to continue to exercise and stay physically fit. Most corporations today rely on monetary coupons or rebates to encourage the purchase of a particular product or service. In the year 2000 over 330 billion coupons were distributed with approximately 4.5 redeemed for a total consumer savings of $3.6 billion. Overall, 77.3% of people use coupons.

Issuance of rewards or incentives to encourage, motivate, or promote additional physical activity or exercise is nothing new. For instance, U.S. Pat. No. 6,585,622 as well as U.S. Published Application Nos. 2005/0102172; 2003/0065561; 2002/0077219 all disclose systems in which rewards are earned based on user participation in physical activity or exercise. Rewards or points are accumulated and may be redeemed at a later point in time. Such systems require the establishment of an infrastructure so that the physical activity of the user may be monitored and the rewards of incentive points issued. In part due to the expense associated with employing such an infrastructure, these systems and methods are best suited for monitoring participation in physical activity or exercise over an extended period of time. Irrespective of the accumulation and tabulation of intangible rewards or points as they are earned over a period of time, such a protracted process is better suited for adults rather than children or teenagers who have a shorter attention span which requires more immediate gratification in today's fast paced society.

It is therefore desirable to develop a new interactive physical coupon, whereby after engaging in physical activity for a predetermined amount and/or predetermined period of time the coupon is activated and immediately redeemable providing the user with immediate satisfaction.

SUMMARY OF THE INVENTION

The present application is directed to an interactive coupon redeemable by the holder after having participated in physical activity for a predetermined period of time.

The application relates to a kinetic coupon for encouraging participation in physical activity. Initially, the kinetic coupon may be inactive when dispensed to the user. While in possession of the kinetic coupon the user participates in physical activity that is monitored by circuitry in the coupon. The circuitry determines when the user's participation in physical activity exceeds a predetermined threshold, e.g., a predetermined amount and/or predetermined period of time. After participating in physical activity that exceeds the predetermined threshold, the kinetic coupon is validated and signified to the user that it is now redeemable.

The application comprises a coupon that detects physical activity of a user using a motion detector. The motion detector may use any one of a variety of technologies such as chemical motion detectors, mechanical motion detectors, or electrical motion detectors.

A chemical motion detector according to the present application may comprise one or more chemicals which, when mixed, indicate to a user that the threshold of activity has been reached. The chemicals may be included in various reservoirs or indicator wells, which mix upon physical activity and movement of the motion detector. The chemicals may also be mixed using micro-pumps, which are powered by movement of the motion detector and dispense the chemicals from one or more reservoirs. In a further embodiment, a piezoelectric device powered by physical activity may be used to power the micro-pumps. The micro-pumps may be configured to function only upon a certain level of physical activity such that minor movements of the motion detector do not drive the micro-pumps.

In another embodiment, a chemical motion detector according to the present application may comprise one or more chemical solutions that react to the sweat, pH level of, biological cues, or chemicals released by or through a user's skin during and after physical activity.

In another embodiment, a chemical motion detector according to the present application may comprise one or more chemicals that are microencapsulated in small spheres that burst upon physical activity. An abrasive agent may be provided adjacent to the spheres to assist in the rupture of the spheres.

A mechanical motion detector according to the present application may comprise a number of different configurations. In one embodiment, the motion detector comprises a pendulum which moves upon physical activity of the user and causes the rotation of a ratchet gear. Once the ratchet gear has been moved a sufficient number of times, the user is presented with the indicator. Another embodiment of a mechanical motion detector to be used with the present application is a magnetic switch in which a metal ball is held in place using magnetic attraction. Physical activity of the user will force the metal ball to move and short against a contact, which is detected and used to determine when the threshold of physical activity has been reached.

Another embodiment of a mechanical motion detector comprises a conductive tube in which a conductive object such as a metal ball is disposed. A spring inside the conductive tube maintains the ball apart from a contact at the end of the tube. Motion such as physical activity of the user causes the ball to compress the spring and short against the contact at the end of the tube, which is registered by a circuit which determines when the predetermined threshold of activity has been reached.

In a further embodiment of a mechanical motion detector which may be used with the present application, a conductive element such as a ball is disposed in a bounded area on a conductive plate and surrounded by a conductive wall or conductive posts. The wall or posts are separated from the conductive plate such that the ball will close a circuit between the wall or posts and the plate when the ball touches the wall or posts. Upon physical activity of the user, the ball moves inside the bounded area and closes a circuit between the wall or posts and the plate whenever it touches them both. The bounded area may be flat and elongated in a certain direction to detect only one range of motion. The bounded area may also be a sphere in order to detect motion in every direction. The different posts may register different signals with the circuitry so that the present application may detect a predetermined threshold of various different types of physical activities which cause different motions of the motion detector. In some embodiments, a dampening device surrounds the ball in order to eliminate the detection of minor movements that do not constitute physical activity which the present application seeks to detect.

Another embodiment of a mechanical motion detector comprises a conductive pin, wire, or ribbon which may have a conductive weight on the free end. Spaced from the weight in various different directions are contact points which close a circuit upon contact with the weight. While the motion detector is not moving, the weight is not contacting any other surface, but physical activity will cause the weight to move and contact one or more contact points disposed a predetermined distance from the weight.

The coupon according to the present application has an indicator which indicates to the user when a certain threshold of physical activity has been reached. The indicator may be a change in color of the coupon, the appearance of an image or message on the coupon, a visual indicator such as a light emitting diode, or a sonic indicator.

Once the predetermined threshold of physical activity has been detected by the coupon, the coupon may be redeemed. In one embodiment, the coupon may be redeemed by bringing the coupon to a location such as a retail store or restaurant which accepts the coupon in exchange for free or discounted goods and/or services. In another embodiment, the coupon may be redeemed on an interactive web site by, for example, entering a unique code from the coupon into the web site. The unique code may be electronically revealed on a display such as, for example, a liquid crystal display or a series of light emitting diodes. The unique code may also be permanently printed on the coupon or printed on the coupon in a way that reveals all or a portion of the unique code once the predetermined threshold of physical activity has been reached. The coupon may be redeemed for users to earn free or discounted goods and/or services.

In one embodiment, the coupon is a single-use product that may be discarded upon redemption. In another embodiment, once the coupon has reached the predetermined threshold of physical activity and redeemed, it may be reset so that it may be used again. In this embodiment, the vendor who issued and collected the coupon may reset the coupon for repeated distribution.

BRIEF DESCRIPTION OF THE FIGURES

The foregoing and other features of the present application of the present application will be more readily apparent from the following detailed description and drawings of illustrative embodiments of the application wherein like reference numbers refer to similar elements throughout the several views in which:

FIGS. 3a and 3b are front and side views, respectively, of an exemplary device employing chemical technology for monitoring the extent of participation in physical activity or movement by the user;

FIG. 3c is a front view of the device in FIGS. 3a and 3b with the membrane deformed;

DETAILED DESCRIPTION

Figure 1:
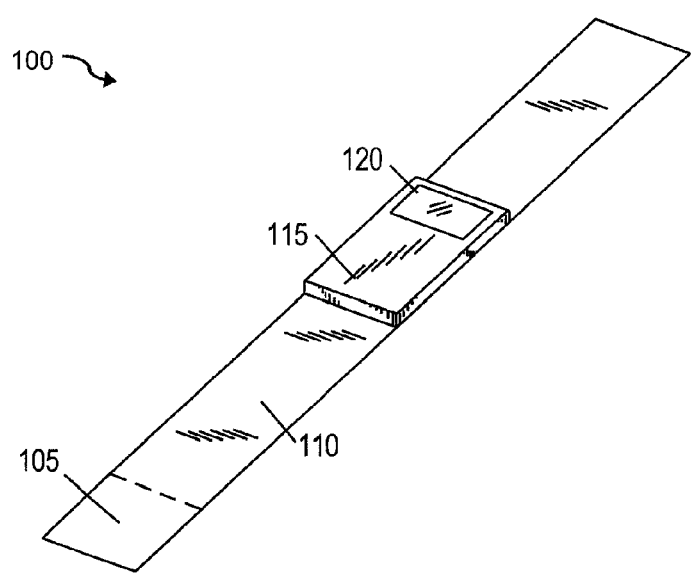
FIG. 1 is a enlarged perspective view of the exemplary kinetic coupon in accordance with the present application.

The present application is directed to an interactive or "kinetic" coupon that is a physical device which is redeemable, activated or validated only after the user has participated in movement or physical activity of a predetermined amount and/or for a predetermined period of time. Referring to FIG. 1, the kinetic coupon 100 has a housing 115 in which is enclosed components for monitoring the extent of physical activity or movement by the user and activating an indicator to signify to the user when the kinetic coupon is redeemable, activated or validated. A display 120 such as, for example, a light emitting diode (LED), liquid crystal display (LCD) or other display device is provided for display of some type of indicia indicating when the physical activity exceeds a predetermined threshold, i.e., a predetermined amount and/or predetermined period of time. The indicator may simply be a color indicator (e.g., change from colorless to a color, change of color or change from opaque to transparent to reveal some indicia otherwise not previously visible). For instance, after participating in physical activity for a predetermined period of time, a green color may be indicated on the display 120. Alternatively, written indicia may be observed in the display 120. Any desired alphanumeric word or message may be displayed. In one embodiment, the written indicia may display some sort of encouragement such as "Keep Going", "Don't Stop" before the predetermined time period has expired in which the user has participated in physical activity or movement. Once the wearer has participated in physical activity for the predetermined threshold the indicia is activated to reflect the redeemable value of the coupon and/or perhaps the location at which the coupon is to be redeemed. By way of example, upon engaging in physical activity or movement for the predetermined period of time, the display 120 may read "Free Frisbee" and the name of the participating vendor from whom the toy may be redeemed. The kinetic coupon may alternatively, or in addition to a visual indicator, include an audible alarm and associated circuitry for producing an audible alarm. Upon the engagement of physical activity that exceeds the predetermined threshold, the kinetic coupon will produce or generate an audible sound to inform the wearer that the coupon may now be redeemed. Such audible alarm may be a beep, melody, word, phrase or instructions as to how to go about redeeming the value of the coupon.

A coupon according to the present invention may comprise a voucher, rebate, ticket, lottery or sweepstakes entry, certificate, token, IOU, note, etc.

The coupon may be redeemable on an interactive web site for free or discounted goods and/or services. The coupon may, for example, display a code when the predetermined threshold has been reached. The coupon may also display a code which will only be accepted by a vendor once the coupon provides indication that the threshold level of physical activity has been reached. The user may then enter the code into the web site to be redeemed.

Figure 2:
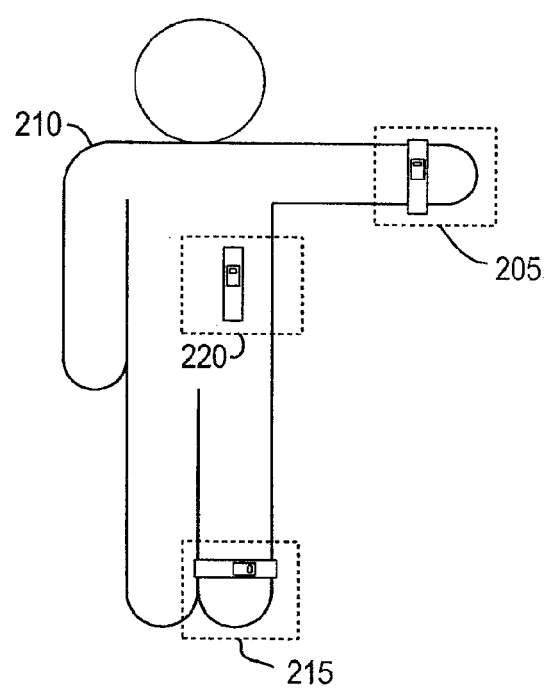
FIG. 2 is an exemplary kinetic coupon in accordance with the present application shown being worn on different parts of the body.

Kinetic coupon 100 may be secured about a part of the body, for example, by a band or strap 110. FIG. 2 shows several exemplary positions of the kinetic coupon 100 worn on the body of a wearer 210, e.g., about the wrist 205 or ankle 215. Other parts of the body may be chosen such as, but not limited to, the head, earlobe, neck, arm, finger, leg, toe, or waist of the wearer 210. As shown in FIG. 1, the strap 110 may also include a securing device 105. The securing device 105 may be, but need not necessarily be, releasable such as hook-n-eye, VELCRO™, a buckle, a snap or a clasp. In the case that the securing device 105 is not releasable, then the strap may be broken or torn after use and discarded either alone or with the housing 115 and components disposed therein. Yet another variation of the present application would eliminate the securing device 105 altogether whereby the strap would be made of a material such as a thin metal or plastic band that in a relaxed state is wound into a coil, but upon the application of a force may be stretched out substantially straight. After being positioned about a portion of the body, the force exerted on the band is removed allowing it to return to its relaxed state and substantially conform about a part of the body of the wearer 210. The strap may be custom designed and printed, as desired, for instance, to identify a corporate name and/or promotional item or an advertiser.

Alternatively, the strap 110 itself may also be eliminated and the kinetic coupon 100 releasably secured directly to the body or clothing of the wearer 210 via an adhesive strip, pin or other device. This alternative embodiment is particularly well suited for placement of the kinetic coupon on the wearer 210 rather than about a part of the body of the wearer 210, such as depicted in FIG. 2 by coupon 220 worn on the chest of the wearer 210. Instead of being worn on or about the body or clothing of the wearer 210, the wearer 210 may simply hold the kinetic coupon in their hand.

As previously mentioned the coupon 100 includes components for indicating when the user's participation in physical activity or movement exceeds a predetermined threshold, e.g., a predetermined amount and/or predetermined period of time, required to activate or validate the coupon. The kinetic coupon may be designed to require either continuous or non-continuous physical activity or movement. Functionality for monitoring the extent of the user's participation in physical activity or movement may be achieved using chemical, mechanical and electrical technology either exclusively or in combination thereof. It is advantageous to minimize the cost of manufacture and overall size when designing the components for monitoring the extent of participation in physical activity or movement by the user. An illustrative example of a system for monitoring the extent of user's participation in physical activity or movement utilizing each of the three different technologies will be described, however, alternative devices such as piezoelectric devices or pedometers are contemplated and within the intended scope of the present application.

The first method to be addressed employs chemical technology whereby one or more chemicals when mixed together activate an indicator that signifies to the user participation in movement for at least a predetermined threshold, e.g., predetermined amount and/or predetermined time period. Referring to FIGS. 3a and 3b, indicator wells 305 are filled with a chemical indicator that is activated when mixed with fluid from a reservoir 310. In the illustrative example shown, the coupon includes three indicator wells 305, each having three indicator apertures illustrated therein via the circular elements within the indicator wells 305, wherein each indicator aperture represents a different indicator (e.g., different color or indicia such as a letter or number). An impervious membrane 315 covers the surface of the device and is sealed around a pump 320 to form a vacuum. The pump 320 such a micro-pump is used to dispense fluid from reservoir 310. A fluid is selected based on such factors as its potential corrosive effects and viscosity to pass through the pump. In the exemplary embodiment three pumps 320 are shown, one associated with each well indicator 305. The application may be modified, as desired, to vary the number of indicator wells, indicator apertures and/or pumps.

An external force such as a motor or piezoelectric device may be used to drive the micro-pump. However, the use of a motor or piezoelectric device disadvantageously requires a power source that contributes to both the overall cost of manufacture and footprint of the integrated circuit. In a preferred embodiment, the use of a power source is eliminated altogether and instead the micro-pumps are driven by an oscillating membrane that acts as a piston. The user's motion thereby supplies the necessary force to drive the micro-pump. Accordingly, a predetermined minimum threshold level of physical activity or movement may be required to drive the micro-pump. Some physical activity or movement may be so inconsequential as to be insufficient to drive the micro-pump. Some physical or movement may be so inconsequential as to be insufficient to drive the micro-pump. As the user moves, the mass of the fluid in pumping well 350 causes the membrane 315 to vibrate or oscillate and deform, as shown in FIG. 3c. The pumping action of mass or magnet 340 may be enhanced by utilizing a changing magnetic field or a fluctuating mass. Specifically, as shown in FIG. 3c a magnetic field is created by the displacement of a magnet 340 with respect to an attracting material 345 such as steel or other magnetic material disposed proximate the pump 320. The attracting material 345 shown in FIG. 3c is configured in the shape of a metal ring. in operation, the user's motion causes the membrane 315 to vibrate or oscillate by the mass of the fluid flowing into the pumping well 350 from reservoir 310 resulting in an initial displacement of magnet 340. As the magnet 340 approaches the metal ring 345 the attraction of magnetic forces assist the suction of fluid from the reservoir 310 into the pump well 350. Gravity and motion forces the fluid into the indicator wells 305.

Reducing channels or reserve flow restrictors 330, 335 are preferable used to create a unidirectional flow of fluid from the reservoir 310 to each of the indicator wells 305. As the mass or magnet 340 is displaced in a positive y-direction a vacuum forces liquid to flow from the reservoir 310 into the pumping well. Micro-pump 320 provides metered output based on the type of movement or physical activity. The mass of magnet 340 is selected based on different activity levels. The orifice of the flow restrictors may be adjusted to accommodate a wide variety of flow rates and fluids. Fluids stored in reservoir 310 may be neutral, acidic or alkaline. The indicator in wells 305 may be a solid, fluid, gas or some combination thereof which when it mixes with the fluid from reservoir 310 is activated. In one embodiment the indicator wells activate the indicator immediately upon contact with fluid dispersed from the reservoir, irrespective of the amount of fluid. However, an alternative embodiment provides for activation of the indicator by a predetermined amount of fluid from the reservoir passing into the indicator well. This latter embodiment may be employed to signify that a period of time for participation by the user in physical activity or movement has expired. Exemplary indicators such as fluids, gels or paper that may be used include halochromic chemical compound that produce changes in compounds such as Thymol blue, Methyl red and Indigo carmine. Another class of fluid is Amylose in starch which can be used to produce a blue color in the presence of iodine. The iodine molecule slips inside of the amylose coil. Iodine is not very soluble in water, therefore the iodine reagent is made by dissolving iodine in water in the presence of potassium iodide to produce a soluble linear triiodide ion complex. The triiodide ion slips into the coil of the starch creating a blue-black color.

Figure 7A:
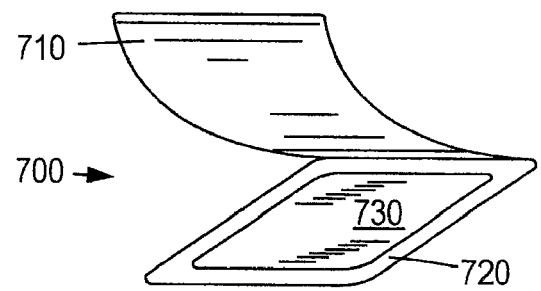
FIGS. 7a and 7b depict one embodiment of a motion-activated coupon according to the present application.
Figure 7B:
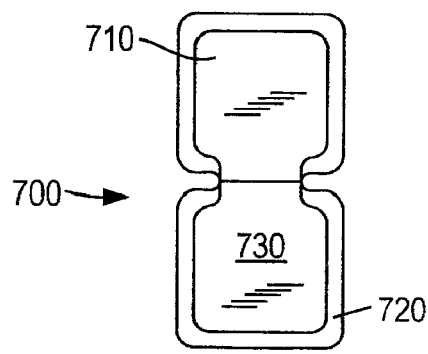

In one embodiment, the coupon comprises one or more chemical solutions that react to motion, sweat, and/or pH level of the user's skin during and after a physical activity. The chemical solutions may cause a portion of the coupon to change from one color to another. The chemical solutions may also transform an opaque overlay to a transparent overlay to reveal a layer of printed information below the layer. One example of this embodiment is the coupon 700 depicted in FIGS. 7a and 7b. Coupon 700 has a first layer 710 which may contain a message or image and a second layer 720 with an overlay 730 that will transform from opaque to transparent upon the physical activity that activates the chemical solutions. The transparent window will then allow the user to view the message on the first layer 710.

In one embodiment, the coupon comprises two or more chemicals that react to movement of the coupon. One or more of the chemicals may be microencapsulated in small spheres and react to the second part of the solution that has an abrasive. The abrasive, with time and physical agitation, will break the encapsulated spheres and mix the two chemicals. One or more of the solutions will then change from one color to another or from an opaque overlay to a transparent overlay to reveal a layer of printed information below the overlay.

In one embodiment, the coupon comprises two gels which begin mixing when a seal separating them is broken. The physical agitation from the user will mix the two gels over a predetermined amount of time. Once the two gels have sufficiently mixed, they will then change from one color to another or from an opaque overlay to a transparent overlay to reveal a layer of printed information below the overlay.

Figure 4:
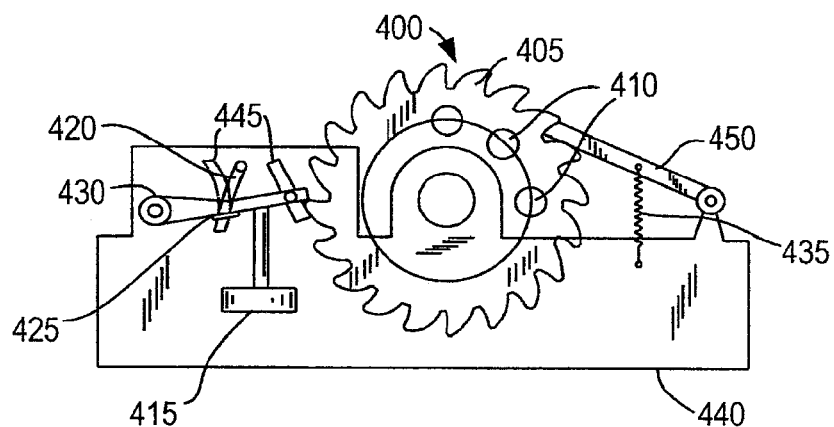
FIG. 4 is a schematic diagram of an exemplary device employing mechanical technology for monitoring the extent of participation in physical activity or movement by the user.

The next methodology to be discussed is use of the mechanical technology whereby mechanical components are displaced by forces generated by or derived from the user's motion to indicate when the user has engaged in physical activity or movement for a predetermined threshold, e.g., a predetermined amount and/or predetermined period of time. A pendulum is employed that swings when the user moves. Guides 445 serve as an escapement mechanism to restrict movement to a single direction. FIG. 4 is an exemplary assembly 400 that includes a ratchet gear 405 rotatably mounted on a base 440. A weight 415 freely supported by a level or arm 430 serves as a pendulum. The user's motion is imparted to weight 415 which, in turn, displaces the lever or arm 430 engaging a tooth of the ratchet gear 405 causing it to rotate. A rubber band 420 produces a balancing or restoring force. Hinge 425 allows the lever or arm 430 to pivot between a downward stroke position in which it engages a tooth of the ratchet gear 405 and another position a predetermined distance clear of the gear when the restoring force generated by the rubber band 420 pulls the arm back to its original position. Indicator apertures 410 may be provided to enable a mark to be visually observed by the user to signify when the user has engaged in a predetermined amount of physical activity or movement.

In the case of the present inventive kinetic coupon being utilized as an incentive for children to engage in physical activity to promote a healthier lifestyle, it is often desirable to ignore or disregard physical activity or movement by the user that is inconsequential or insignificant so as not to contribute towards the issuance or earning or rewards or points. Therefore the present application may be designed so that the motion exerted by the user is not recorded until it exceeds a predetermined threshold level. There are numerous methods in which said functionality may be accomplished an example of which will be described in further detail.

Referring once again to the mechanical assembly shown in FIG. 4, motion exerted by the user is not recorded until it overcomes or exceeds a counterbalancing static force exerted on the ratchet gear 405. This counterbalancing static force may be produced by a tension spring 435, a magnet or other device. Rotation of the ratchet gear 405 is restricted by a restricting arm 450 which is pivotally mounted to base 440. The tension spring 435 is connected between the base and restricting arm 450. When the user's motion overcomes or exceeds the counterbalancing static force produced by the tension spring physical activity or movement is recorded.

Figure 8A:
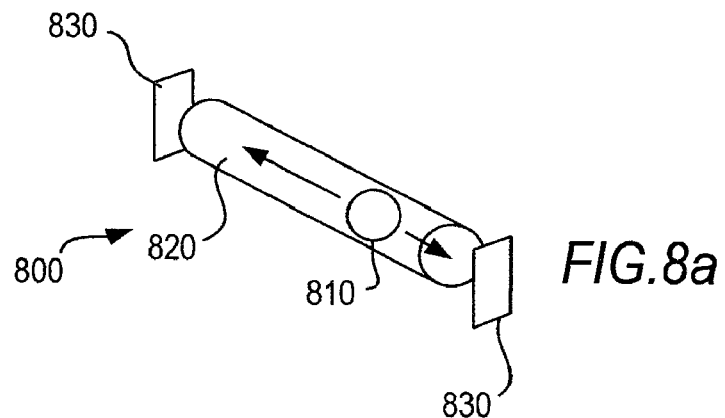
FIGS. 8-18b depict embodiments of motion sensors to be included with coupons according to the present application.

In one embodiment, the coupon comprises a kinetic device as a sensor which comprises a magnetic switch. The magnetic switch may include a conductive object such as, for example, a metal ball which is held in place in an area by magnetic attraction. If the force is strong enough the object will overcome the magnetic force of the object, which will move to either end of the area and short against two contacts at the boundaries of the area. The shorting of the contacts may be detected to assess physical activity. FIG. 8a depicts one example of this a motion sensor 800 according to this embodiment in which the magnetic ball 810 is held by magnetic attraction between the contacts 830 in the tube 820.

Figure 8B:
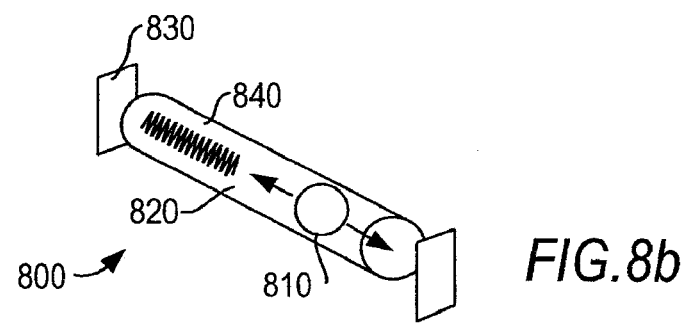

In one embodiment, the coupon includes a motion sensor composed of a conductive tube inside of which resides a conductive object such as a ball and a coil. FIG. 8b depicts a motion sensor 800 according to one example of this embodiment. One end of the tube 820 contains an electrical contact 830 insulated from the tube. A coil 840, compression spring, or other compressible, non conductive material rests on the insulted portion of the electrical contact 830 located in the end of the insulted tube 820 and holds the conductive ball 810 from the end of the conductive tube 820. Upon sensing motion, the ball 810 deflects inside tube 820 in the general direction of the motion. This compresses the spring 840 and, if the motion is of sufficient magnitude, causes the ball 810 to come in contact with the contact 830 at the end of the conductive tube 820. Coming in contact with the electrical contact 830 in the end of the tube 820 causes an electrical circuit to be made. This circuit signal is interpreted by control electronics indicating that motion has occurred. The circuit signal may include a electronic circuit that incorporates algorithms capable of detecting individual deflections and interprets the inputs to correspond to the use, orientation and numeric quantity of deflections detected. The electronics interpret the information and send the results to a storage or enunciation device which may include a display such as, for example, liquid crystal display, light emitting diode display or other means to store or communicate the resulting information to a user.

Figure 8C:
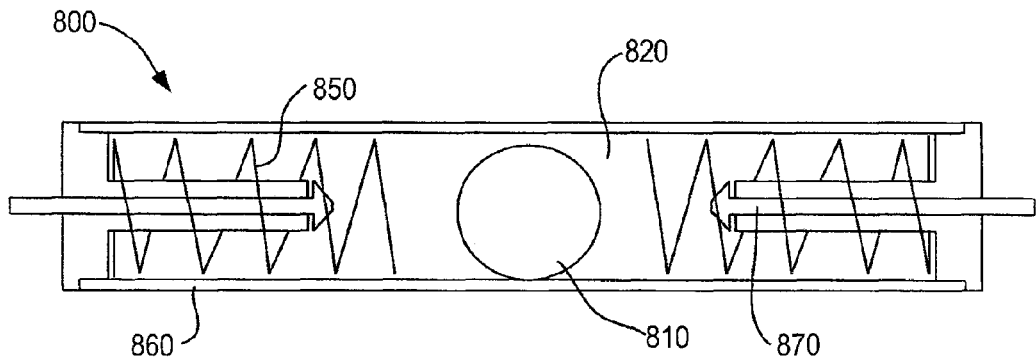

In one embodiment, the coupon comprises a spring-loaded ball and multiple contact tube motion detector. The motion sensor may be composed of a conductive tube inside of which resides a conductive ball. Each end of the tube contains an electrical contact insulated from the tube. Two coil compression springs or other compressible material rest on the insulated portion of the electrical contact located in the end of the insulated tube and hold the conductive ball equidistant from the ends of the conductive tube. Upon sensing motion, the ball deflects inside tube in the general direction of the motion. This compresses the spring and, if the motion is of sufficient magnitude, causes the ball to come in contact with the contact at the end of the conductive tube. Coming in contact with the electrical contact in the end of the tube causes an electrical circuit to be made. This circuit signal is interpreted by control electronics indicating that motion has occurred. One example of this embodiment is depicted in FIG. 8c. The conductive ball 810 is housed in the conductive tube 860 between two springs 850. The springs surround two conductive posts 870 and hold the conductive ball 810 away from the two conductive posts 870 while the motion detector 800 is standing still. Motion of the motion detector 800 will force the conductive ball 810 against one of the springs 850 which will compress and allow the conductive ball to touch one of the conductive posts 870 which completes a circuit with the conductive tube 860. Each time a circuit is completed, the circuitry of the coupon implements a counter until the predetermined threshold is reached.

Figure 9:
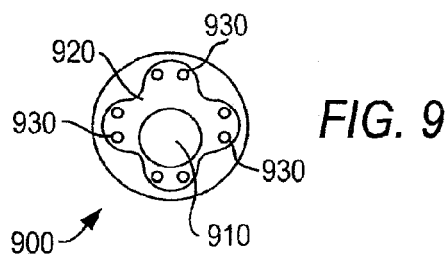

In one embodiment, the coupon comprises a dual-axis motion sensor with a ball in a cross-shaped channel. One example of this embodiment is depicted in FIG. 9. In this embodiment, the motion sensor 900 comprises a conductive sphere 910 and rests inside a cross-shaped channel 920. The shape of the channel fixes the potential movement of the ball 910 to two axes. At the end of each of the four channels there is an electronic contact 930 that closes a circuit whenever the ball 910 makes contact. The cross-shaped channel form and orientation to the device is defined by the orientation and the allowed movement.

Figure 10:
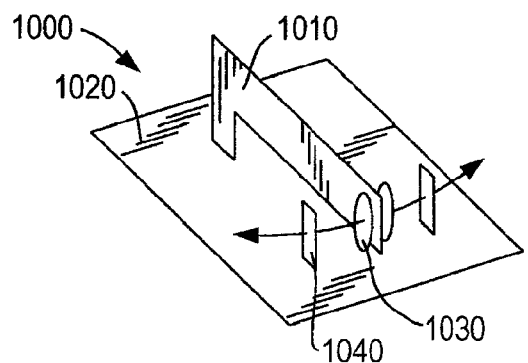

In another embodiment, the coupon comprises a single-axis motion sensor. One example of this embodiment is depicted in FIG. 10. The motion sensor 1000 is comprised of a single conductive flat spring 1010 in which one end is affixed to a circuit board 1020 or other conductive member and the other end contains a weight 1030 to amplify detected motion. Conductive stops 1040 are affixed to the circuit board 1020 and are equally spaced on either side of the flat spring 1010 and weights 1030. Upon deflection, the conductive flat spring 1010 contacts conductive stops 1040. When contact with the conductive stops 1040 occurs, a signal flows through the circuit board 1020 or other conductive member to the sensor then to the conductive stops and back through the circuit board. This signal is interpreted by control electronics indicating that motion has occurred. The conductive stops may be electrically joined or remain separate wherein the control electronics may interpret the signal received from the motion detector together or individually.

Figure 11:
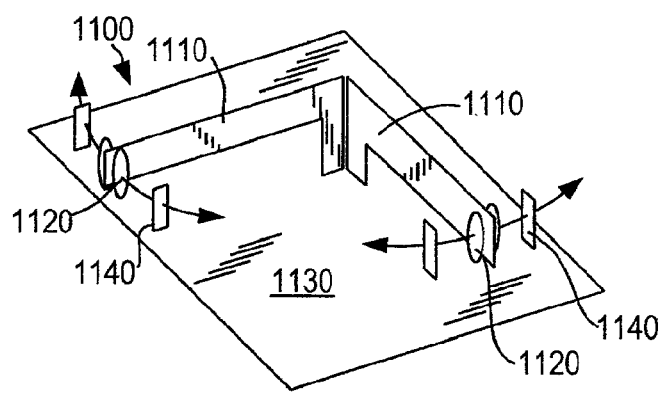

In one embodiment, the coupon comprises a dual-axis motion sensor comprised of a single conductive flat spring bent to form an angle of between 1 and 90 degrees. One example of this embodiment is depicted in FIG. 11. Each end of the flat spring 1110 incorporates a weight 1120 to amplify detected motion. The bent end of the sensor 1110 is affixed to a circuit board 1130 or other conductive member. Conductive stops 1140 are affixed to the circuit board and are equally spaced on either side of the flat springs 1110 and weights 1120. When contact with the conductive stops 1140 occurs, a signal flows through the circuit board 1130 or other conductive member to the sensor then to the conductive stops 1140 and back through the circuit board 1130. This signal is interpreted by control electronics indicating that motion has occurred. Each of the four conductive stops 1140 may be electrically joined or remain separate. Therefore, the control electronics may interpret the signal received from the motion detector 1100 together or individually. In this embodiment, the motion detector may include an electronic circuit that incorporates algorithms capable of detecting and interpreting individual or joined signals from the motion sensor. The electronics can define orientation, number of deflections from each conductive stop and interpret the results. The resulting information is maintained in electrical storage or displayed on an enunciation device which may include a Liquid crystal display, Light emitting diode display or other means to store or communicate the resulting information to a user.

Figure 12:
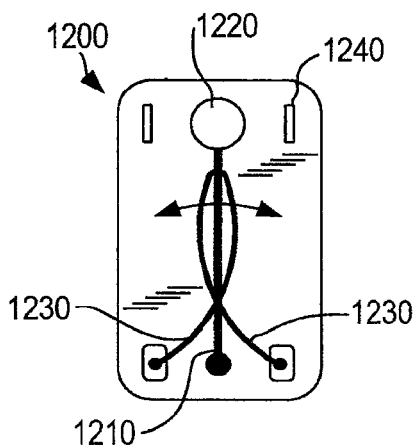

In one embodiment as depicted in FIG. 12, the coupon comprises a motion sensor having a dual-axis or balanced pendulum motion detector 1200 composed of a pendulum 1210 which pivots at one end and contains a weight 1220 at the other, and which incorporates two balanced hair pin springs 1230 symmetrically located around the long axis of the pendulum 1210. The hair pin springs 1230 balance the pendulum 1210 in a central location and allow deflection in two directions. Two contacts 1240 are located at either side of the pendulum weight 1220. Deflection of the pendulum 1210 to either contact 1240 causes an electrical circuit to be completed between the pivot end of the pendulum 1210 through the weight 1220 to either contact 1240. The contacts 1240 may be joined or separated. The pendulum 1210 may include electronic logic. This embodiment may further comprise an electronic circuit that incorporates algorithms capable of detecting individual or joined deflections and interpreting the inputs to correspond to the use, orientation and numeric quantity of deflections detected. The electronics interpret the information and send the results to a storage or enunciation device which may include a Liquid crystal display, Light emitting diode display or other means to store or communicate the resulting information to a user.

Figure 13:
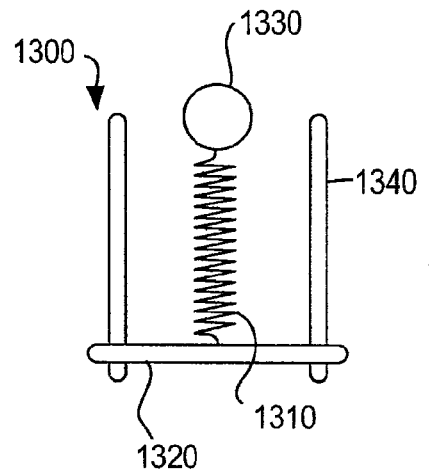

In one embodiment as depicted in FIG. 13, the coupon comprises a motion detector 1300 comprising a spring wire 1310 with a dampening device motion detector. This embodiment includes a three-axis motion sensor 1300 in which a conductive spring 1310 wire is affixed to a selectively conductive mounting plate 1320 (such as a printed circuit board) and the other end incorporates a fixed weight 1330. A predetermined length of the spring wire 1310 protrudes through a compressible material (such as open cell foam). The fixed weight end 1330 protrudes through a conductive hoop 1340. The hoop 1340 is connected to the mounting plate 1320. Upon deflection, the conductive spring wire 1310 deflects and contacts the conductive hoop 1340. When contact with the conductive hoop 1340 occurs, a signal flows through the printed circuit 1320. This signal is interpreted by control electronics indicating that motion has occurred. The conductive hoop may be electrically joined or remain separate wherein the control electronics may interpret the signal received from the motion detector. This embodiment may include electronic logic such as, for example, an electronic circuit that incorporates algorithms capable of detecting individual deflections and interpreting the inputs to correspond to the numeric quantity of deflections detected. The electronics send the resulting information to a storage or display device such as, for example, a liquid crystal display, light-emitting diode display or other means to store or communicate the resulting information to a user.

In one embodiment, the coupon comprises a spring wire with dampening device motion detector and three-axis interpretation. This embodiment includes a three-axis motion sensor in which a conductive spring wire is affixed to a selectively conductive mounting plate (such as a printed circuit board) and the other end incorporates a fixed weight. A predetermined length of the spring wire protrudes through a compressible material (such as open cell foam). The fixed weight end is located between two individual contacts. A third contact is located on the selectively conductive mounting plate under the weight. Upon sensing motion, the spring wire is deflected and contacts one or more of the conductive contacts. An electrical signal flows through the selectively conductive mounting plate. This signal is interpreted by control electronics indicating that motion has occurred. The conductive stops may be electrically joined or remain separate wherein the control electronics may interpret the signal received from three contacts and the motion detector. The compressible material dampens oscillations from the spring wire. This motion detector may include an electronic circuit that incorporates algorithms capable of detecting individual deflections and interpreting the inputs which correspond to the use, orientation and numeric quantity of deflections detected. The electronics interpret the information and send the results to a storage or enunciation device which may include a Liquid crystal display, Light emitting diode display or other means to store or communicate the resulting information to a user.

In one embodiment, the coupon includes a motion detector that can detect 360 degrees of longitudinal motion and which is comprised of a platform with a single outer raised conductive ring, an inner conductive surface placed inside, but not contacting the raised conductive ring, a movable ball or "puck" is located inside the raised conductive ring, and a compressible porous member such as open cell foam, which fits around the movable ball or "puck" and which is compressed by the ball or "puck" as it is deflected by motion. The ball or "puck" is held in a central location by the compressible porous member. Upon sensing motion, the ball or "puck" is deflected and causes the porous member to compress in the direction the motion is detected and proportion to the energy contained in the motion. If the energy is sufficient, the porous member if fully compressed and the ball or puck makes contact through the porous member to the raised conductive ring. Making contact with the raised conductive ring caused an electrical circuit to be completed. This embodiment may include an electronic circuit that incorporates the algorithms capable of detecting deflections and interpreting the inputs to correspond to the use, orientation and numeric quantity of deflections detected. The electronics can define orientation, number of deflections from each conductive stop and interpret the results. The resulting information is maintained in electrical storage or displayed on a display device such as, for example a liquid crystal display, light-emitting diode display or other means to store or communicate the resulting information to a user.

Figure 14:
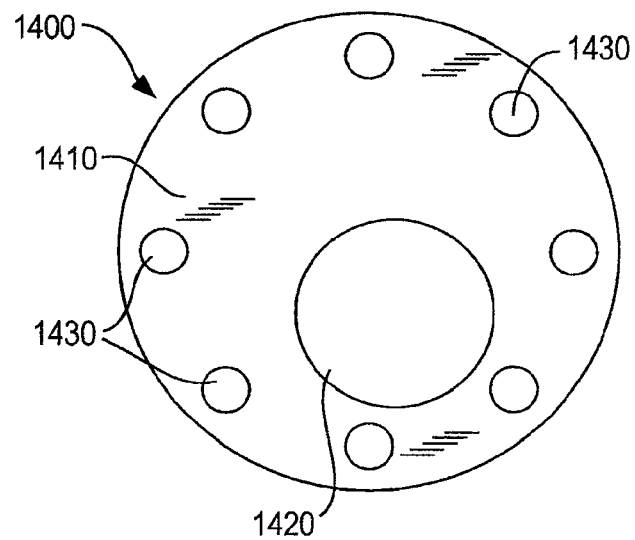

In one embodiment as depicted in FIG. 14, the coupon includes a motion sensor 1400 comprising separate or individual raised conductive ring members 1430 arranged equidistant from a center point and mounted on a platform 1410, an inner conductive surface is located on the platform but not touching the raised conductive ring members 1430, a movable ball 1420 or "puck" is located inside the individual raised conductive ring members 1430, and a compressible porous member which fits around the movable ball 1430 or "puck" and which is compressed by the ball 1430 or "puck" as it is deflected by motion. The ball 1430 or "puck" is held in a central location by the compressible porous member. Upon sensing motion, the ball 1430 or "puck" is deflected and causes the porous member to compress in the direction the motion is detected and proportion to the energy contained in the motion. If the energy is sufficient, the porous member if fully compressed and the ball 1430 or puck makes contact through the porous member to one or more of the individual raised conductive ring members 1430. Making contact with one or more individual raised conductive ring members 1430 caused an electrical circuit to be completed. This motion sensor 1400 may include a electronic circuit that incorporates algorithms capable of detecting individual or joined deflections and interpreting the inputs to correspond to the use, orientation and numeric quantity of deflections detected. The electronics send the resulting information to a storage or enunciation device which may include a Liquid crystal display, Light emitting diode display or other means to store or communicate the resulting information to a user.

Figure 15A:
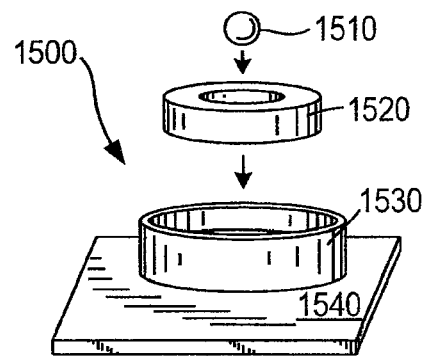
Figure 15B:
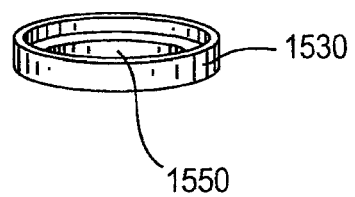
Figure 15C:
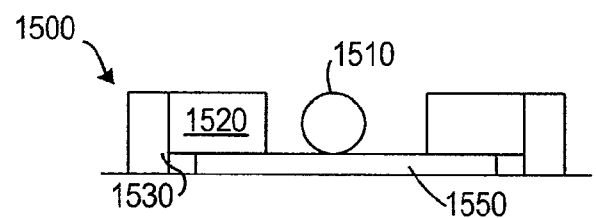
Figure 15D:
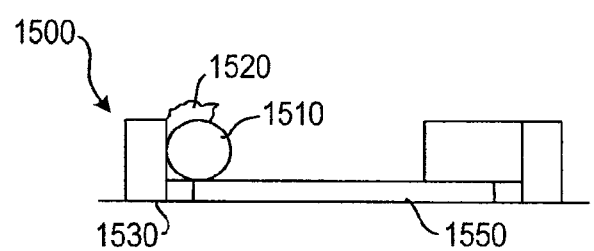
Figure 15E:
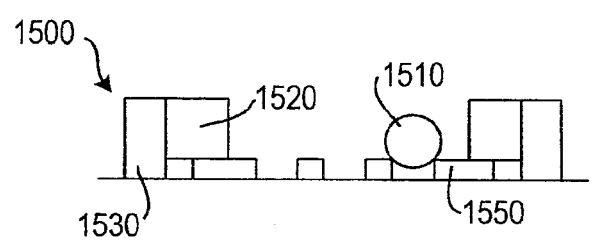

As depicted in FIGS. 15*a*-15*e*, one embodiment of the present application comprises a coupon including a motion detector 1500 comprising a conductive element such as a ball 1510, a dampening element such as a foam ring 1520, and a conductive ring 1530 disposed on a substrate 1540. The conductive ring 1530 surrounds an inner conductor 1550. A cross-section of this motion detector 1500 is depicted in FIG. 15c which shows the ball 1510 resting on the inner conductor 1550 and held apart from the conductive ring 1530 by the foam ring 1520. As depicted in FIG. 15d, motion of the motion detector will force the ball 1510 against the foam ring 1520, deforming the foam ring 1520 and forming a circuit between the inner conductor 1550 and the conductive ring 1530. In a further embodiment depicted in FIG. 15e, the inner conductor 1550 may have channels, holes, or protuberances which inhibit the free movement of the ball 1510 and thus require additional motion to form a circuit.

Figure 16:
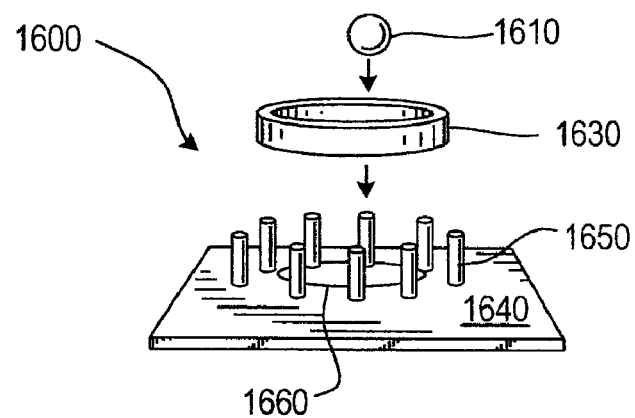

A similar embodiment of a motion detector 1600 is depicted in FIG. 16 in which a conductive element such as a ball 1610 is disposed in a dampening element such as a foam ring 1630 which is placed inside a number of conductive posts 1650 on a substrate 1640. An inner conductor 1660 is disposed in the middle of the motion detector 1600. In this embodiment, the ball 1610 forms a circuit between the conductive posts 1650 and the inner conductor 1660 when the ball 1610 is subject to sufficient motion to deform the foam ring 1630 and allow the ball 1610 to contact the conductive posts 1650 while resting on the inner conductor 1660.

Figure 17:
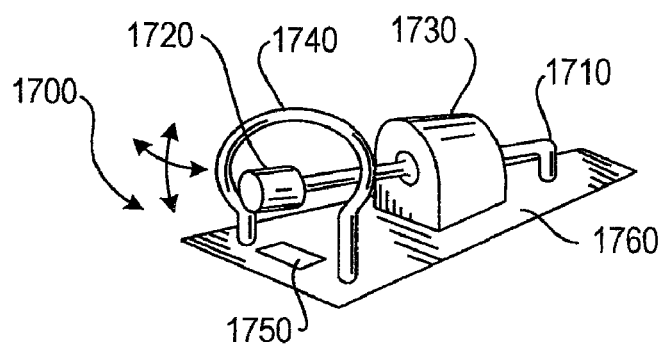

FIG. 17 depicts another embodiment of a motion detector 1700 to be included with a coupon according to the present application. The motion detector 1700 comprises a conductive pin 1710 that may have a weight 1720 coupled to the end. The conductive pin 1710 may be surrounded by a dampening element such as a piece of foam 1730 which may be coupled to the substrate 1760 from which the conductive pin 1710 extends. The weight 1720 is surrounded by a conductive member 1740 and/or a conductive plate 1750. The movement of the motion detector 1700 will cause the weight 1720 to contact either the conductive member 1740 or the conductive plate 1750, closing a circuit with the conductive pin 1710.

Figure 18A:
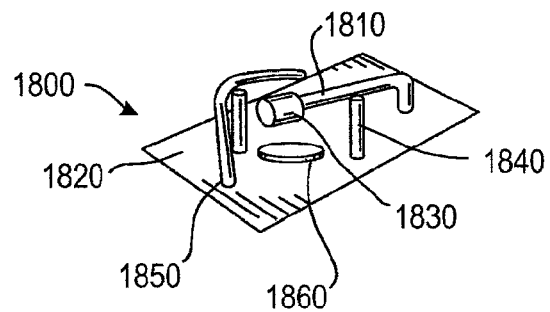
Figure 18B:
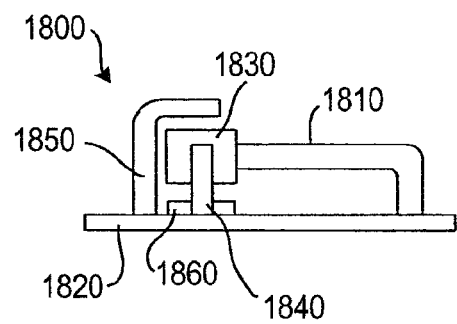

A similar embodiment is depicted in FIG. 18a. In this embodiment of a motion detector 1800, a conductive pin 1810 with a weight 1830 extends from a substrate 1820. The weight 1830 is surrounded by a plurality of conductive posts, 1840, 1850 and positioned above a conductive plate 1860. Motion cause the conductive pin 1810 to contact either the posts 1840, 1850 or the conductive plate 1860 which completes a circuit. A side view of this embodiment is depicted in FIG. 18b.

Figure 19:
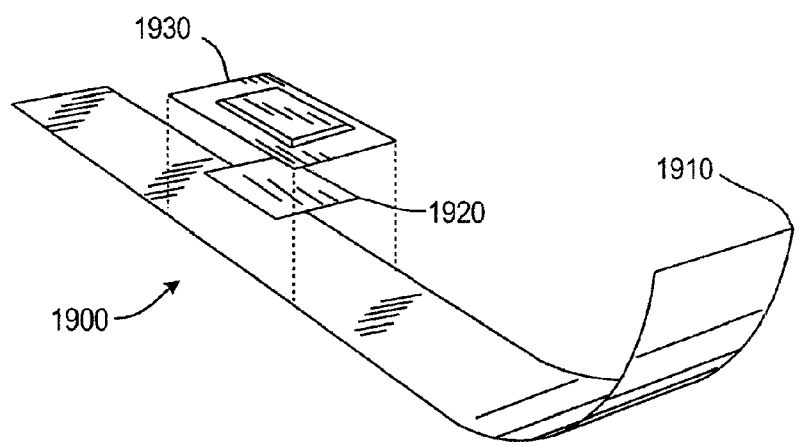
FIG. 19 depicts one embodiment of a coupon according to the present application coupled to a wearable device.

One embodiment of a coupon is depicted in FIG. 19. The coupon 1900 comprises a flexible band 1910, a circuit 1920 which includes a motion detector, and a housing 1930 which holds the circuit 1920 to the flexible band 1910. The flexible band 1910 may further comprise an adhesive strip on one or both ends in order to affix the coupon 1900 to a user. In some embodiments, the housing 1930 may be a pocket in the band 1910 and not a separate component. In another embodiment, the housing 1930 may also be coupled to the sensor and then affixed to the band 1910.

In one embodiment, the coupon comprises a motion detector comprised of individual contacts arranged on a sliding surface and which are spaced equidistant from a center point and which alternate in conductivity. A ball or puck is contained inside the contacts and which upon being tilted, slides against the contacts and creates a circuit. The sensor can detect tilts at 45 degree quadrants.

In one embodiment, the coupon comprises a ring motion detector with equidistant non-alternating contacts. The motion detector is comprised of individual contacts arranged on a sliding surface and which are spaced equidistant from a center point and which do not alternate in conductivity (i.e. ++, −−). A ball or puck is contained inside the contacts and which upon being tilted, slides against the contacts and creates a circuit. The sensor can detect tilts at 90 degree quadrants.

In one embodiment, the coupon comprises a ring motion detector with equidistant pairs of alternating contacts. The motion detector is comprised of pairs of contacts arranged on a sliding surface and which are spaced equidistant from a center point and the contact of which alternate in conductivity. A ball or puck is contained inside the contacts and which upon being tilted, slides against the contacts and creates a circuit. The sensor can detect tilts at 45 degree quadrants. Space between alternating contacts changes speed and transition of the ball or puck from one set of contacts to the other.

In one embodiment, the coupon comprises a motion detector comprised of pairs of contacts arranged on a sliding surface and which are spaced equidistant from a center point and the contact of which do not alternate in conductivity. A ball or puck is contained inside the contacts and which upon being tilted, slides against the contacts and creates a circuit. The sensor can detect tilts at 90 degree quadrants.

In either of the ring designs described above, a hole may exist in the center of the ring surface (i.e. printed circuit board). This will allow the ball or puck to remain idle or in a stationary position during a time when the motion detector should not be registering hits (i.e. during transportation).

In another embodiment, the motion detector is comprised of pairs of electrical contacts arranged around the circumference of a sliding surface. A plurality of holes or protuberances are incorporated into the sliding surface. A conductive object such as, for example, a sliding puck or rolling ball, touches the electrical contacts upon tilting of the motion detector and creates electrical contact between the contacts. The holes or protuberances in the sliding surface alter the friction between the conductive object and the surface thereby adjusting the reaction of the conductive ball or puck to tilting. When the conductive object contacts one or more of the electrical contacts, a circuit is formed between the contacts and the contact is recorded by a device.

Figure 5:
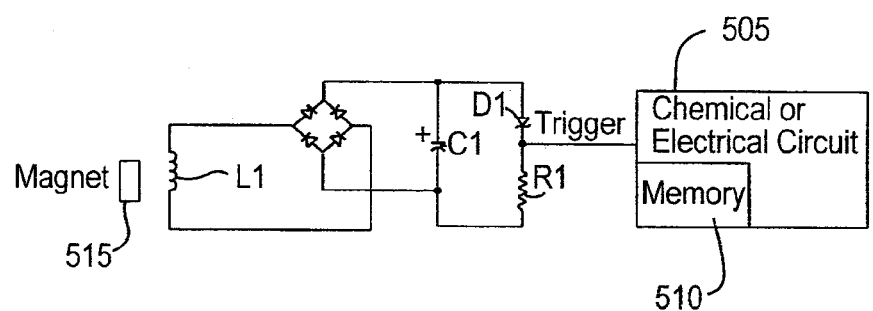
FIG. 5 is a schematic diagram of an exemplary device employing electrical technology for monitoring the extent of participation in physical activity or movement by the user.

A final and third methodology for monitoring the user's motion is achieved using electrical technology, as shown in FIG. 5. In accordance with this third method electrical energy is captured by moving a magnet 515 around or through a coiled wire. A change in the magnetic field includes an electromotive force or voltage in inductor L1. Four diodes denoted as D1 represent a bridge rectifier to convert the AC voltage generated in inductor L1 to DC voltage for storage by a capacitor C1. Similar to that described above with respect to the other methodologies, the electrical methodology also disregards physical activity or movement by the user which is inconsequential or insignificant (falls below a predetermined threshold level). To achieve this result, a triggering signal is transmitted to power ON a chemical or electrical circuit 505 only when the stored voltage in capacitor C1 exceeds a predetermined threshold voltage level of physical activity or movement. In the ON state, the voltage is used to power the circuit 505 to electronically record the level of physical activity in a memory 510 and change the pH of a compound of a chemical indicator thereby producing a color to signify to the user that the kinetic coupon has been validated or activated and is now redeemable.

It is to be noted that each of the methodologies described above may be used independently or in any combination thereof.

Many additional features may be added to the inventive kinetic coupon. A timing clock may be employed to ensure that the kinetic coupon is validated and/or redeemed after being validated prior to expiration of a predetermined redemption period of time. Upon the expiration of the predetermined redemption period of time, the kinetic coupon if not yet validated will no longer be activatable and, if already validated, will become inactive or perhaps indicate on the display that it is no longer redeemable.

The kinetic coupon may be reusable whereby after validation and redemption the components may be reset and used again. Otherwise, it is also contemplated and within the intended scope of the application for all or some portion of the kinetic coupon to be disposable. One factor in this determination is the overall cost associated with the components of the kinetic coupon itself.

As previously noted, the kinetic coupon may be designed or customized, as desired, to promote the specific corporation or sponsor. For example, the name, trademark, logo, or other indicia of the corporation or sponsor may be displayed on the strap or other portion of the coupon including in the display itself. In this regard, the kinetic coupon may be used as yet another advertising tool for promotion of a corporate or sponsor's name, brand, and/or product/service. Additional companies or advertisers may be added to the kinetic coupon.

Figure 6:
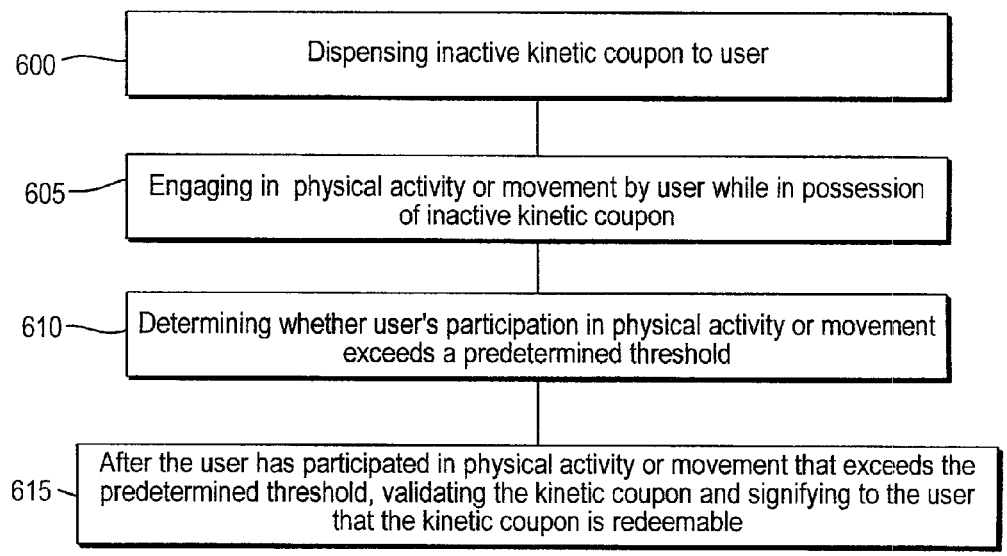
FIG. 6 is an exemplary flow chart of the use of the kinetic coupon in accordance with the present application.

FIG. 6 is an exemplary flow chart of the user of the kinetic coupon in accordance with the present application. In step 600 in inactive coupon is dispensed to the user. Initially, the kinetic coupon is not activated and this not redeemable for any type of reward or incentive. However, the indicia may display instructions that invite the user to participate in physical activity or movement while in possession of the inactive kinetic coupon in step 605. A determination is made in step 610 whether the user's participation in physical activity exceeds a stored predetermined threshold, e.g., a predetermined amount of physical activity and/or a predetermined period of time. After the user has participated in physical activity for at least the predetermined threshold then in step 615 the kinetic coupon is validated and signifies to the user that it is now able to be redeemed.

Thus, while there have been shown, described, and pointed out fundamental novel features of the application as applied to a preferred embodiment thereof, it will be understood that various omissions, substitutions, and changes in the form and details of the devices illustrated, and in their operation, may be made by those skilled in the art without departing from the spirit and scope of the application. For example, it is expressly intended that all combinations of those elements and/or steps that perform substantially the same function, in substantially the same way, to achieve substantially the same results be within the score of the application. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book, or any other reference cited herein is each incorporated by reference in their entirety.

We claim:

1. A method for redeeming a coupon upon completion of a predetermined threshold of physical activity, comprising:
    issuing a coupon that comprises a kinetic device having one or more motion sensors configured to monitor motion associated with the kinetic device and detect whether the monitored motion indicates that the predetermined threshold of physical activity has been reached;
    receiving a request to redeem the coupon at an interactive web site; and
    processing the request to redeem the coupon at the interactive web site based on whether the motion monitored with the one or more motion sensors indicates that the predetermined threshold of physical activity has been reached.

2. The method of claim 1, wherein processing the request to redeem the coupon includes accepting the coupon in exchange for free or discounted goods or services in response to the motion monitored with the one or more motion sensors indicating that the predetermined threshold of physical activity has been reached.

3. A method for redeeming a coupon upon completion of a predetermined threshold of physical activity, comprising:
    issuing a kinetic coupon device having one or more motion sensors configured to monitor physical activity associated with a user wearing or holding the kinetic coupon device and detect whether the physical activity monitored with the one or more motion sensors indicates that the user wearing or holding the kinetic coupon device has completed the predetermined threshold of physical activity;
    receiving a request to redeem the kinetic coupon device at an interactive web site; and
    processing the request to redeem the kinetic coupon device at the interactive web site based on whether the physical activity monitored with the one or more motion sensors indicates that the user wearing or holding the kinetic coupon device has completed the predetermined threshold of physical activity.

4. The method of claim 3, wherein the one or more motion sensors include a chemical motion detector having one or more micro-pumps adapted to dispense and mix chemicals in one or more reservoirs or indicator wells upon movement of the kinetic coupon device to monitor the physical activity associated with a user wearing or holding the kinetic coupon device.

5. The method of claim 3, wherein the kinetic coupon device further includes an indicator to signify that the kinetic coupon device can be redeemed in response to the one or more motion sensors in the kinetic coupon device detecting that the monitored physical activity has reached the predetermined threshold of physical activity.

6. The method of claim 3, wherein the one or more motion sensors include a chemical motion detector having one or more chemicals microencapsulated in one or more spheres and an abrasive agent arranged to rupture the one or more spheres and release the one or more microencapsulated chemicals upon movement of the kinetic coupon device, and wherein physical agitation from the movement of the kinetic coupon device mixes the abrasive agent with the released microencapsulated chemicals over time to produce a solution that changes from one color to another color upon the user completing the predetermined threshold of physical activity.

7. The method of claim 3, wherein the one or more motion sensors include an electrical motion detector having a magnet adapted to move around or through a coiled wire upon movement of the kinetic coupon device, an inductor adapted to capture electrical energy produced from the magnet moving around or through the coiled wire, a capacitor adapted to store voltage converted from the electrical energy captured in the inductor, and an electronic circuit adapted to receive power from the voltage stored in the capacitor and record the physical activity associated with the user wearing or holding the kinetic coupon device upon the movement of the kinetic coupon device exceeding a predetermined minimum threshold level.

8. The method of claim 3, wherein the one or more motion sensors include a mechanical motion detector having a pendulum adapted to swing and cause one or more ratchet gears to rotate upon movement of the kinetic coupon device, a tension spring or magnet adapted to produce a counterbalancing static force that restricts the one or more ratchet gears from rotating until the movement of the kinetic coupon device exceeds a predetermined minimum threshold level, and one or more indicator apertures adapted to reveal a visual mark to signify that the kinetic coupon device can be redeemed upon the completing the predetermined threshold of physical activity.

9. The method of claim 3, wherein the one or more motion sensors include a mechanical motion detector having one or more electrical contacts, a conductive object bounded within a channel, and a circuit adapted to close upon movement of the kinetic coupon device causing the conductive object to move within the channel and short against the one or more electrical contacts.

10. The method of claim 9, wherein the mechanical motion detector further includes a spring arranged within the channel to maintain the conductive object apart from the one or more electrical contacts until the movement of the kinetic coupon device exceeds a predetermined minimum threshold level that causes the conductive object to compress the spring and short against the one or more electrical contacts.

11. The method of claim 9, wherein the channel bounds the conductive object within an area flat and elongated in a certain direction to only detect one range of the movement of the kinetic coupon device.

12. The method of claim 9, wherein the channel bounds the conductive object within a cross-shaped area to detect the movement of the kinetic coupon device in two directions or a spherical area to detect the movement of the kinetic coupon device in every direction.

13. The method of claim 3, wherein the one or more motion sensors include a mechanical motion detector having a conductive plate, one or more conductive walls or posts separated from the conductive plate, a conductive object disposed in a bounded area on the conductive plate and surrounded by the one or more conductive walls or posts, and a circuit adapted to close upon movement of the kinetic coupon device causing the conductive object to move within the bounded area and simultaneously touch the conductive plate and the surrounding conductive walls or posts.

14. The method of claim 3, wherein processing the request to redeem the kinetic coupon device includes:
accepting the request to redeem the kinetic coupon device at the interactive web site in response to the request including a unique code that the kinetic coupon device reveals upon the user wearing or holding the kinetic coupon device completing the predetermined threshold of physical activity; and
resetting the kinetic coupon device in response to accepting the request to redeem the kinetic coupon device at the interactive web site, wherein resetting the kinetic coupon device enables the kinetic coupon device to be redeemed again in response to the one or more motion sensors again detecting that the predetermined threshold of physical activity has been reached.

15. The method of claim 3, wherein the kinetic coupon device reveals a unique redemption code on a display associated with the kinetic coupon device in response to the one or more motion sensors indicating that the user wearing or holding the kinetic coupon device has completed the predetermined threshold of physical activity.

16. The method of claim 15, wherein processing the request to redeem the kinetic coupon device includes accepting the request to redeem the kinetic coupon device at the interactive web site in response to the request including the unique redemption code.

17. The method of claim 5, wherein the indicator comprises a chemical solution adapted to transform an overlay portion of the kinetic coupon device from opaque to transparent in reaction to motion, sweat, or a skin pH level to reveal printed information signifying that the kinetic coupon device can be redeemed.

18. The method of claim 13, wherein the bounded area has an orientation flat and elongated in a certain direction to only detect one range of the movement of the kinetic coupon device or a spherical orientation to detect the movement of the kinetic coupon device in every direction.

19. The method of claim 3, wherein the one or more motion sensors include a mechanical motion detector having a spring that protrudes through a compressible material that dampens oscillations from the spring, a conductive mounting plate affixed to the spring, one or more conductive hoops connected to the conductive mounting plate, and a circuit adapted to close upon movement of the kinetic coupon device causing the spring to deflect and contact the one or more conductive hoops to trigger a signal that flows from the one or more conductive hoops to the conductive mounting plate.

20. The method of claim 4, wherein the chemical motion detector further includes a piezoelectric device or an oscillating membrane configured to drive the one or more micropumps upon the movement of the kinetic coupon device exceeding a predetermined minimum threshold level.

21. The method of claim 5, wherein the indicator comprises a display device configured to display an image or written indicia to visually signify that the kinetic coupon device can be redeemed in response to the one or more motion sensors in the kinetic coupon device detecting that the monitored physical activity has reached the predetermined threshold of physical activity.

22. The method of claim 21, wherein the display device is further configured to display one or more encouragement words or messages in response to the physical activity monitored with the one or more motion sensors indicating that the user wearing or holding the kinetic coupon device has not completed the predetermined threshold of physical activity.

23. The method of claim 5, wherein the indicator comprises sonic circuitry configured to produce an alarm to audibly signify that the kinetic coupon device can be redeemed in response to the physical activity monitored with the one or more motion sensors indicating that the user wearing or holding the kinetic coupon device has completed the predetermined threshold of physical activity.

24. The method of claim 23, wherein the one or motion sensors detect that the user wearing or holding the kinetic coupon device has completed the predetermined threshold of physical activity in response to detecting that the user has participated in the monitored physical activity until a predetermined time period expires.

* * * * *